United States Patent [19]

Jaffe

[11] 4,035,150

[45] July 12, 1977

[54] TEST FOR OCCULT BLOOD IN AN EMULSIFIED AQUEOUS/ORGANIC SYSTEM

[75] Inventor: Russell M. Jaffe, Greenbelt, Md.

[73] Assignee: The United States of America as represented by the Secretary of the Department of Health, Education and Welfare, Washington, D.C.

[21] Appl. No.: 703,244

[22] Filed: July 7, 1976

Related U.S. Application Data

[63] Continuation-in-part of Ser. No. 616,129, Sept. 24, 1975, abandoned, and a continuation-in-part of Ser. No. 498,109, Aug. 16, 1974, abandoned.

[51] Int. Cl.$^2$ .................. G01N 31/22; G01N 33/16
[52] U.S. Cl. ............................. 23/230 B; 23/259; 210/359; 210/500 M; 210/DIG. 23; 210/DIG. 24
[58] Field of Search .................................. 23/230 B

[56] References Cited

U.S. PATENT DOCUMENTS 3,865,548   2/1975   Padarver ...................... 23/230 B X

OTHER PUBLICATIONS

Ingham, "An Improved and Simplified Benzidine Test for Blood in Urine and Other Clinical Material," Biochemical Journal, vol. 26, (1932), pp. 1124–1126.
Henry, "Clinical Chemistry Principles and Technics," pp. 779–782, (1964).
Kohn et al., "Inhibition of the Benzidine Blood Test by Ascorbic Acid," J. Biol. Chem., vol. 124, pp. 163–168, (1938).
Stas, M. E., "Het Aantonen Van Bloed in Faeces," Ned. Tijdschr. Geneesk, vol. 97, pp. 1709–1710, (1953).
Dent, "Occult–Blood Detection in Faeces of Various Animal Species," Lab. Pract., 1973, 22(11), pp. 674–676. Anal. Abst., 210, vol. 27, No. 1, July 1974.

*Primary Examiner*—Norman Yudkoff
*Assistant Examiner*—Barry I. Hollander
*Attorney, Agent, or Firm*—John S. Roberts, Jr.; Norman J. Latker; Thomas G. Ferris

[57] ABSTRACT

A method and test of detecting occult blood in a stool or other physiologic fluid sample which offers novelty in that the reaction is carried out in the organic phase selected from the group consisting of methylene dichloride, petroleum ether, and dioxane in an aqueous/organic bi-phase system wherein the sample of occult blood is added to the aqueous phase, the bi-phase system is mixed by emulsification and a standard color-forming reaction involving organically soluble hemoglobin (heme), peroxide, and dye is carried out in the organic phase. Optionally, a filter paper porous only to organic solvents may be introduced to initially separate the aqueous and organic phases and further a device for mixing and separating immiscible liquids having two chambers telescopable into one another may be utilized. The reaction involving hemoglobin is carried out in acetic acid to produce heme which is later solubilized by the organic solvent. An advantage over previous tests lies in the effectiveness of the present method even in the presence of normally occurring amounts of ascorbic acid which inhibit all aqueous phase methods. The present test will give positive results for occult blood in the presence of at least 20 mg/dl of ascorbic acid (Vitamin C) or, alternatively, where the patient has ingested levels of Vitamin C or other reducing agent at an input of above 6 gm/day orally. This latter factor is quite important in present-day clinical practice where a substantial percentage of the patients are ingesting Vitamin C.

4 Claims, 7 Drawing Figures

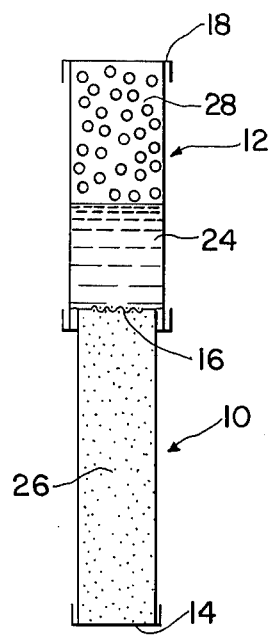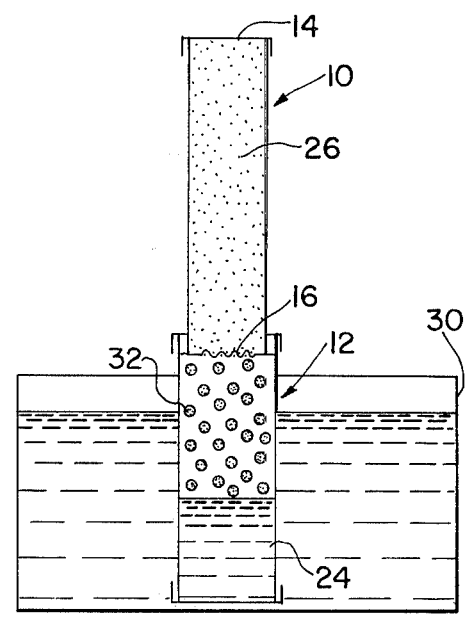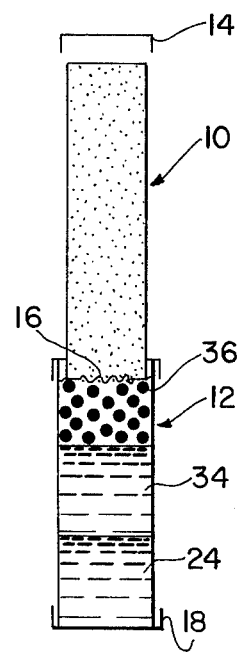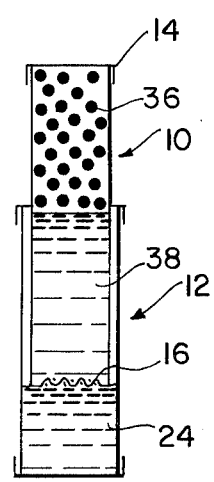
FIG. 2A   FIG. 2B   FIG. 2C   FIG. 2E   FIG. 2D

TEST FOR OCCULT BLOOD IN AN EMULSIFIED AQUEOUS/ORGANIC SYSTEM

This is a continuation-in-part application of Ser. No. 498,109, filed Aug. 16, 1974 now abandoned, and Ser. No. 616,129, filed Sept. 24, 1975 now abandoned.

The present invention involves or relates to an improved method of testing for occult blood and a resulting test kit for facilitating same. Occult blood is defined as blood present in such small quantities that it can be detected only by chemical tests of suspected material or microscopic or spectroscopic examination (Dorland's Medical Dictionary, 24th Edition, W. B. Saunders, 1974).

In the prior art there is a history of related procedures as follows:

1. John Ingham, "An Improved and Simplified Benzidine Test for Blood in Urine and Other Clinical Material," *Biochemical Journal*, 26:1124–1126, 1932. In urine and in feces (pages 1125–26) the author strongly recommends that the ethereal extract be evaporated and the residue subsequently tested. This leads away from applicant's invention. It is noted that peroxide free ether will not support the dye reaction (see Table 1 below). Peroxide free ether became available about 1950 which was subsequent to Ingham's work above. [See *Encyclopedia of Chemical Technology*, 5:862–870 (1950)]. Ingham's positive results on the "ether phase" likely represent artifacts due to peroxide contaminants in his ether of 1932.

TABLE 1
Results of Occult Blood Testing Using Ether Extraction

| | ETHER EXTRACTION | | DRY RESIDUE REHYDRATED |
|---|---|---|---|
| SPECIMEN | Superoxide Free Ether | Superoxide Containing Ether | Superoxide Containing Ether |
| 1:5,000 | Neg | Tr | 1+ (weak) |
| 1:2,000 | Neg | Tr | 2+ |
| 1:1,000 | Neg | Tr | 4+ (strong) |
| 1: 500 | Neg | 1+ | 4+(strong) |
| 1: 100 | Neg | 1+ | 4+ (strong) |
| 0: 100* | Neg | Tr | Neg |

*water to water instead of blood to water

The results above indicate that superoxide containing ether gave false readings due to artifacts or contaminants.

2. Henery, *Clinical Chemistry Principles and Technics*, Chapter 21, subsection "Urine," pages 779–782 (1964). Relative to sensitivity of blood in urine, the author states that interference by ascorbic acid in urine can be avoided by acidification with acetic acid, extraction of resultant acid hematin into ether, evaporation, and performing the test on the residue. Again, in describing the specific tests for specificity at page 781, the author additionally says to acidify the sample with acetic acid, extract the resultant acid hematin into ether or ethyl acetate, evaporate, and test the residue. This would imply that as of 1964 the test was made on the residue and not on the liquid as in the present invention.

3. Stas, "Indication of Blood in Feces," *Biochemistry in the Clinic*, N.T.V.G. 97.II.26, June 27, 1953, pages 1709–10. In describing tests on feces, Stas treats the sample with acetone, then adds glacial acetic acid mixed with ethyl acetate 1:3 and the mixture is concentrated to evaporation. Testing for blood by glacial acetic acid and benzidine is made on the rehydrated residue.

In general, the test kits and methods of the prior art utilizes a combination of ingredients utilized in aqueous solution and generally consisting of a dye, a peroxide, a buffering mix including an organic and an alkali acetate.

In contrast to the prior art, the present invention lies in a method of conducting the detection or color-forming reaction for the occult blood in an organic layer of a two-phase aqueous/organic system wherein interference from reducing agents such as ascorbic acid is screened out and a test will read positive even though a patient has ingested 6 grams or more of ascorbic acid (Vitamin C) orally per diem.

The generalized reaction scheme upon which the present test is based is as follows:

Hemoglobin (or Hematin) + HAc → Globin + Heme

Heme 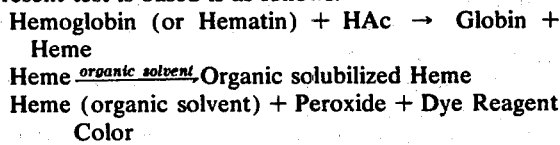 Organic solubilized Heme

Heme (organic solvent) + Peroxide + Dye Reagent Color

Heme in the above is the non-protein insoluble iron protoprophyrin consitituent of hemoglobin denoted by $C_{34}H_{33}O_4N_4FeOH$ and constitutes the pigment portion of the hemoglobin molecule. The oxidation of the iron in the heme by the peroxide followed by the transfer of oxygen from the oxidized iron to the dye reagent (benzidine) produces the color change denoting a positive test for occult blood.

The reagents for the test and method include:

1. Water, saline or 2% sodium dodecyl sulfate (or similar detergent)
2. 30% acetic acid or 10% sulfuric or similar acid
3. Ethyl acetate or similar organic solvent
4. 3% hydrogen peroxide or other peroxide
5. Color reagent (benzidine dihydrochloride, o-dianisidine, o-tolidine, 3,3 dimethylbenzidine, and A.T.B.S.) The color reagent is made of 1 gram starting material dissolved in 20 ml glacial acetic acid diluted to 100 ml with 90% ethanol (or 90% methanol or 90% butanol or 90% propanol).

In the above, as to (3), the organic solvent preferred varieties include lower alkylesters such as ethyl acetate, methylene dichloride, petroleum ether, and dioxane. Examples or organic solvents which are not useful are DMSO and DMF. The proportions for the aqueous phase/organic phase are 10:1 to 1:10 and an optimum ratio is 2:1 aqueous/organic.

As to (4) above, hydrogen peroxide is preferred, but the inorganic peroxides, such as strontium and barium peroxides, may be used as well as the prior art hydroperoxides noted in U.S. Pat. No. 3,012,976 at column 4, lines 68-74, hereby incorporated by reference.

The acid environment utilized to solubilize the heme is preferably at 20% by volume acetic acid but may be any of a variety of organic acid such as citric, fumaric, itaconic, maleic, malic, malonic, and mandelic, with the exception of formic which is not operable.

The color reagent as above may be selected from those utilized above as well as methyl benzthazolinone and leukoindophenols.

In the variation of the test procedure where a filter paper is utilized, it is important that it be of the type which passes organics and refuses aqueous. Such a paper is known in the trade as the Reeve-Angel.

An examplary procedure or method for utilizing this invention is as follows:

A blood sample is added to 3 ml H₂O in a test tube, emulsified, and heated in a boiling water bath for about 5 minutes. Subsequently, the aqueous sample is cooled to room temperature, centrifuged at 500 g for 3 minutes. Post centrifuge, 1 ml of supernatant fluid is withdrawn and added to 3 ml of ethyl acetate in a glass screw-capped vial. The vial is shaken for 15 seconds and allowed to settle, resulting in two phases. A sample (1 ml) of the top layer (ethyl acetate) is withdrawn and placed in a 5 ml glass. To this sample of organic layer is added 1 ml of a dye reagent (e.g., benzidine . HCl), 0.5 ml peroxide (e.g., $H_2O_2$) which is allowed to react for 3–5 minutes and the color is read visually.

BRIEF DESCRIPTION OF THE DRAWINGS

With reference to FIGS. 1 and 2A–2E,

FIG. 1 is a sectional view of an embodiment in accordance with the invention.

FIGS. 2A–2E are schematic views showing a preferred use for the device of Fig. 1.

Figure 1:
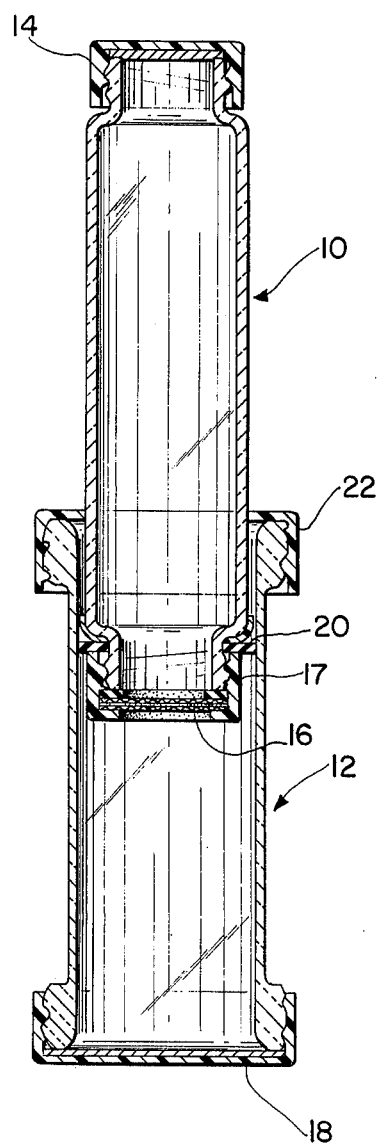

In the embodiments of FIG. 1, the device is comprised of an upper open-ended chamber or container 10 telescopically received in a lower open-ended chamber or container 12. The chambers are preferably formed of an inert and transparent material such as glass. The chamber 10 is closed at its upper end with a cap 14 threaded thereon to sealably close that end of the container.

A filter 16 is disposed across the lower end of the chamber 10, held in place in the embodiment illustrated by an annular threaded cap 17. The filter 16 is of a type which passes organics and refuses aqueous.

The lower end of the lower chamber 12 is closed by a cap 18 threaded thereon to seal that end of the chamber. An annular seal 20 is disposed around and in sealing engagement with the lower end of the chamber 10 and in sliding sealing engagement to the interior wall of the chamber 12 such that a sliding seal is provided therebetween. The seal may be made from any elastomer which is inert, compatible with the environment in which the device is to be used, and has suitable flexibility to function as a sliding seal.

An annular cap 22 is threaded on the upper end of the chamber 12 in the embodiment illustrated to serve as a sliding guide for the chamber 10.

As described above, the presence of blood in feces is determined by mixing a sample of the stool to be analyzed with a hydrophase which can be an aqueous acetic acid. The mixture can be incubated, after which an organic phase, ethyl acetate for example, is mixed with the mixture and the resultant phases are allowed to stratify. The phases are then separated and reagents are added to the organic phase wherein a characteristic color change caused by the oxidation of iron in the heme indicates a positive test for occult blood.

This test can be simply accomplished in the above-described kit by placing a hydrophase 24 consisting of 10 parts of a 30% aqueous acetic acid solution and a specimen of the stool to be analyzed (1 part) into chamber 12 as shown in Fig. 2A. The remaining contents of the device in this condition are air 26 in chamber 10 and a mixture of air and vapors from the hydrophase indicated in the drawings by open circles 28.

The device is then inverted, shaken for 15 seconds, and placed in a heating device such as water bath 30 at 95° C for 5 minutes for incubation. In this condition the contents consist of air 26 in the chamber 10, heated hydrophase 24 and heated vapor-enriched air indicate by dotted circles 32 in the lower chamber 12.

Cap 14 is then removed and an organic phase 34 consisting of an organic solvent such as 5 parts of ethyl acetate is added to chamber 10 and teased through the filter 16 into chamber 12 as shown in FIG. 2C. The organic phase 34 could also be added by re-inverting the kit, removing the cap 18, and introducing the ethyl acetate directly into chamber 12. The contents of the device then comprise organic phase 34, hydrophase 24, and air enriched with warm vapor from the hydrophase and vapor from the organic phase 36 indicated by the solid circles in chamber 12.

The cap 14 (or 18 if the solvent is introduced directly into chamber 12) is then replaced and the kit shaken for 15 seconds, at which time the contents as shown in Fig. 2D comprise the aqueous phase 24, an organic phase carrying any blood present in the test specimen 38 and the vapor 36 in the chamber 12.

The cap 14 is then loosened and the chamber 10 is telescoped into the chamber 12 as shown in Fig. 2E such that a sufficient amount of the organic phase 38 (i.e., 2 parts) is forced through the filter 16 into the chamber 10. In this condition the contents of the device comprise the hydrophase 24 in the chamber 12 and the organic phase 38 and vapors 36 in the chamber 10.

With the phase separation accomplished (the aqueous phase having been refused by the filter 16), reagents consisting of 2 parts of 0.5M benzidine and 1 part of 30% hydrogen peroxide are added to the organic phase 38 in the chamber 10. The kit is then shaken to mix the organic phase and the reagent to accomplish the test for occult blood contained therein.

Figure 3:
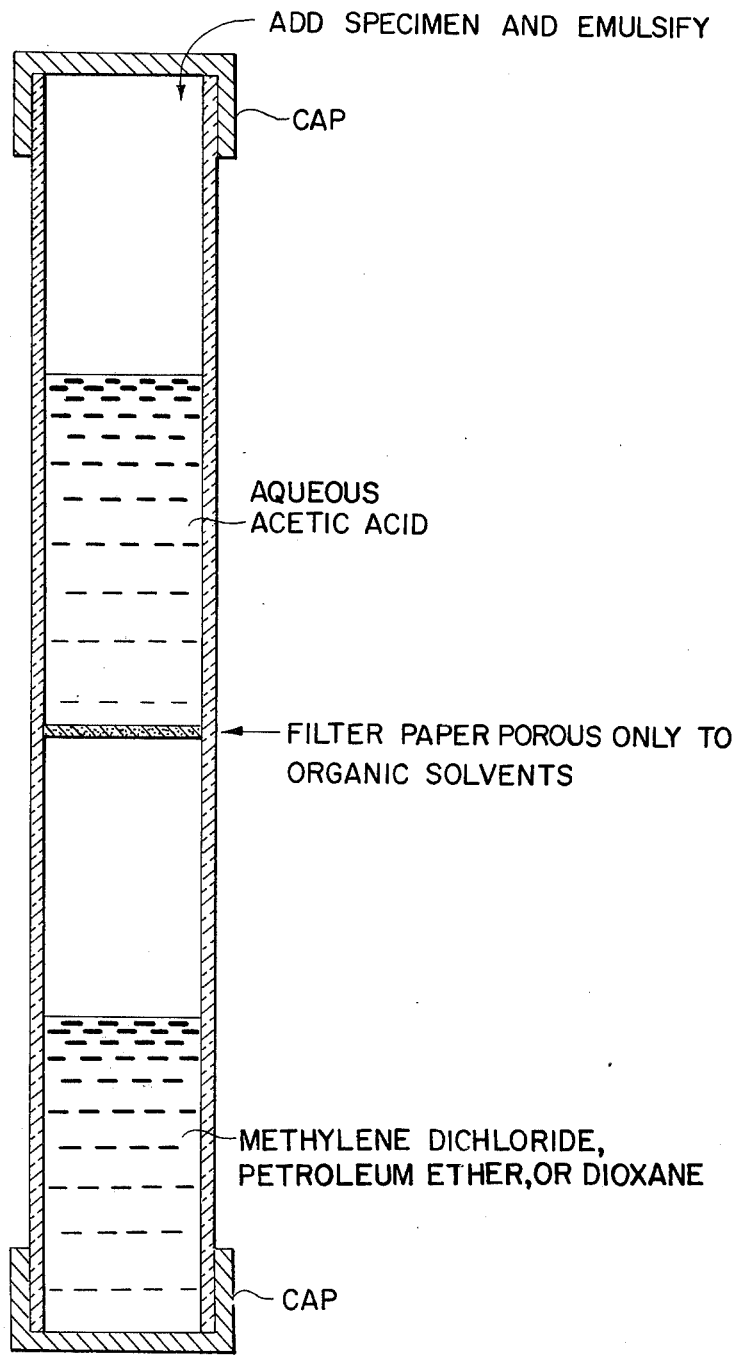
FIG. 3 is a sectional view of an alternative embodiment in accordance with the invention.

In the embodiment of FIG. 3, the drawing is a longitudinal sectional view of an alternative test kit including a filter paper porous only to organic solvents. In this variation the tube is inverted after adding to the tube in the position of the figure the blood specimen and then emulsifying as indicated in the legend of the figure, which allows the organic solvent methylene dichloride, petroleum ether, and dioxane to contact and pass through a filter. The container is shaken and the tube is re-inverted, allowing the organic solvent to return to its compartment, screening out any contaminants in the aqueous phase. The organic solvent side of the container is then uncapped and dye and 0.2 ml 3% $H_2O_2$ is added. Again visual observation for color development is made.

What has been described above is intended as exemplary of a teaching in accordance with the invention to enable those skilled in the art in the practice thereof.

EXAMPLE 1

| In Vitro and Clinical Tests | | |
|---|---|---|
| | Aqueous Phase Occult Blood Testing No. of Pos. | Organic Phase Occult Blood Testing No. of Pos. |
| 250 without ascorbate | 250 | 250 |
| 250 with .05–.10 M ascorbate | 0 | 249 |
| 650 clinical patient samples | 37 | 52* |

*Of the 15 positives by organic phase but not aqueous phase, all were clinically

-continued

| In Vitro and Clinical Tests | |
|---|---|
| Aqueous Phase Occult Blood Testing No. of Pos. | Organic Phase Occult Blood Testing No. of Pos. | positive for occult blood loss. 12/15 were on Vitamin C. Spectrophotometrically blood could be detected in 15/15.

EXAMPLE 2

Comparative Example Clinical

To assess the effect of inhibitory reducing substances such as Vitamin C (ascorbic acid), a prospective clinical trial was undertaken. Five healthy normal volunteers were administered 20 milliliters autologous blood orally. Stool was collected daily for seven-day periods. During certain periods Vitamin C (ascorbic acid) was taken orally from 100 mg three times per day to 2 grams three times per day. Stools were detectably + 24–48 hours after ingestion of blood. Stools remained + for 24–72 hours. At levels up to 250 mg three times per day, aqueous benzidine and the present extraction test were both positive. At 250 mg three times per day the aqueous benzidine test (but not the extraction test) was negatively interfered with. At higher levels the aqueous benzidine test was not reactive; at all levels the extraction test remained positive.

I claim:

1. A method of detecting occult blood in a sample which comprises carrying out the reaction in the organic phase selected from the group consisting of methylene dichloride, petroleum ether, and dioxane of an aqueous/organic bi-phase system wherein a sample of occult blood is added to the aqueous phase, the bi-phase system is emulsified, and a standard color-forming reaction involving solubilized hemoglobin (heme), peroxide, and dye is carried out in the organic phase.

2. The method according to claim 1 wherein the sample contains ascorbic acid.

3. The method according to claim 1 wherein the sample contains at least 20 mg/dl of ascorbic acid.

4. A method of detecting occult blood in a sample which comprises carrying out the detection in an aqueous/organic bi-phase system in which the organic phase is comprised of a solvent selected from the group consisting of methylene dichloride, petroleum ether and dioxane, peroxide and a dye and in which the aqueous phase is comprised of an acid selected from the group consisting of acetic, fumaric, itaconic, maleic, malic, malonic, mandelic, and sulfuric, adding a sample of the occult blood to the aqueous phase whereby blood hemoglobin is hydrolyzed to heme, emulsifying the biphase system to solubilize the heme in the organic phase, oxidize the heme and produce a color change in the presence of the dye reagent.

* * * * *

UNITED STATES PATENT AND TRADEMARK OFFICE
CERTIFICATE OF CORRECTION

PATENT NO. : 4,035,150
DATED : July 12, 1977
INVENTOR(S) : Russell M. Jaffe

It is certified that error appears in the above-identified patent and that said Letters Patent are hereby corrected as shown below:

Col. 1, line 50, change "Henery" to --Henry--.

Col. 2, line 23, insert before "Color", --⟶--.

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*